United States Patent
Pazenok et al.

(10) Patent No.: US 8,455,664 B2
(45) Date of Patent: Jun. 4, 2013

(54) PROCESS FOR PREPARING 1-ALKYL-3-DIFLUOROMETHYL-5-HYDROXYPYRAZOLES

(75) Inventors: Sergii Pazenok, Solingen (DE); Michael Müller, Hilden (DE); Norbert Lui, Odenthal (DE)

(73) Assignee: Bayer CropScience AG (DE)

( * ) Notice: Subject to any disclaimer, the term of this patent is extended or adjusted under 35 U.S.C. 154(b) by 0 days.

(21) Appl. No.: 13/111,582

(22) Filed: May 19, 2011

(65) Prior Publication Data

US 2011/0288304 A1 Nov. 24, 2011

Related U.S. Application Data

(60) Provisional application No. 61/348,361, filed on May 26, 2010.

(30) Foreign Application Priority Data

May 20, 2010 (EP) .................................... 10163420

(51) Int. Cl.
*C07D 231/10* (2006.01)

(52) U.S. Cl.
USPC ..................................................... 548/366.1

(58) Field of Classification Search
USPC ....................................................... 548/366.1
See application file for complete search history.

(56) References Cited

U.S. PATENT DOCUMENTS

| | | | |
|---|---|---|---|
| 2005/0256004 A1 | 11/2005 | Takahashi et al. | |
| 2006/0122399 A1 | 6/2006 | Gonzalez et al. | |

FOREIGN PATENT DOCUMENTS

| | | |
|---|---|---|
| EP | 1 767 528 A1 | 3/2007 |
| EP | 2 128 138 A1 | 12/2009 |
| WO | WO 2007/013536 A1 | 2/2007 |
| WO | WO 2008/093639 * | 7/2008 |

OTHER PUBLICATIONS

International Search Report for International Application No. PCT/EP2011/057828, European Patent Office, Netherlands, mailed Jun. 17, 2011.

* cited by examiner

*Primary Examiner* — Samantha Shterengarts

(74) *Attorney, Agent, or Firm* — Sterne, Kessler, Goldstein & Fox P.L.L.C.

(57) ABSTRACT

The present invention relates to a process for preparing 1-alkyl-3-difluoromethyl-5-hydroxypyrazoles, which are valuable intermediates for the production of fungicides.

21 Claims, No Drawings

PROCESS FOR PREPARING 1-ALKYL-3-DIFLUOROMETHYL-5-HYDROXYPYRAZOLES

The present invention relates to a process for preparing 1-allyl-3-difluoromethyl-5-hydroxypyrazoles, which are valuable intermediates for the production of fungicides.

1-Alkyl-3-difluoromethyl-5-hydroxypyrazoles are important units for preparation of active crop protection ingredients; they are typically prepared by reacting beta-keto esters with alkylhydrazines. This generally forms two regioisomers, which leads to reduced yields. For instance, Takahashi et al. describe, in US2005/256004 A1, the reaction of difluoroacetoacetate with monomethylhydrazine (MMH) to give 3-difluoromethyl-1-methyl-1H-pyrazol-5-ol in the presence of concentrated HCl in ethanol with only 33.3% yield.

Another method for preparing 1-alkyl-3-polyfluoroalkyl-5-hydroxypyrazoles was described by Hamper et al. in J. Fluorine Chemistry, 1990, vol. 48, p. 123-131. The perfluoroalkylacetylene esters used as starting materials are, however, expensive and commercially unavailable.

WO 2007/013536 describes the synthesis of 5-hydroxy-1-alkylpyrazole derivatives by reaction of beta-keto esters which contain. $CF_3-$, for example, with alkylhydrazines in the presence of an acid. This achieved regioselectivities of 82:17 to 98:2. The processes described in the prior art cannot be performed economically due to the low yields and/or the poor access to the reactants needed on the industrial scale. It is therefore an object of the invention to provide an economically viable process which enables the preparation of 1-alkyl-3-difluoromethyl-5-hydroxypyrazoles on the industrial scale.

It has now been found that hydroxy-1-alkyl-3-difluoromethylpyrazoles of the formula (I)

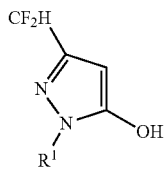

in which $R^1$ is a linear or branched $C_1$-$C_6$-alkyl group are obtained by reacting alkyl difluoroacetoacetates of the formula (II)

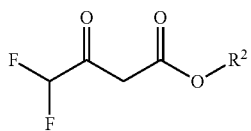

in which $R^2$ is a linear or branched $C_1$-$C_6$-alkyl group, with alkylhydrazines of the formula (III) in the presence of an organic acid and in a solvent.

$NH_2-NH-R_1$      (III)

The process according to the invention can be illustrated by the following formula scheme:

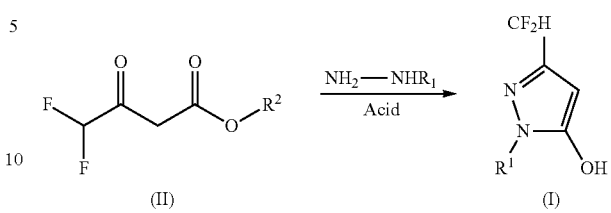

The alkyl difluoroacetoacetates used as starting materials in the performance of the process according to the invention are defined in general terms by the formula (II). The $R^2$ radical in this formula (II) is preferably methyl, ethyl, n-propyl, isopropyl, butyl, pentyl, more preferably methyl and ethyl.

The $R^1$ radical is a linear or branched alkyl group having 1 to 5 carbon atoms, preferably methyl and ethyl.

Organic acids are, for example, formic acid, acetic acid, p-toluenesulphonic acid, trifluoroacetic acid. Preference is given to using formic acid and acetic acid.

Alkyl difluoroacetoacetates of the formula (II) and alkylhydrazines of the formula (III) are known and commercially available.

It is considered to be surprising that the reaction of alkyl difluoroacetoacetates with alkylhydrazines in the presence of an acid proceeds even at low temperatures regioselectively to give the desired 1-substituted pyrazole derivative, while the undesired regioisomeric 2-substituted pyrazole derivative is not formed.

In this context, "regioselective" means that less than 5%, preferably less than 1%, more preferably less than 0.1%, of the undesired regioisomer is formed.

The reaction temperatures in the performance of the process according to the invention can be varied within a range from 0° C. to 60° C. Preference is given to working at temperatures of 20° C. to 40° C., particular preference to working at room temperature.

Depending on the reactivity of the reactants, the reaction time may be up to 30 hours, though the reaction can also be stopped earlier in the event of full conversion. Preference is given to reaction times of 8-20 hours.

In the performance of the process according to the invention, generally between 0.8 and 1.8 mol, preferably between 1 and 1.5 mol, of alkylhydrazine of the formula (III) and 0.1 to 1.2 mol of the organic acid are used per mole of alkyl difluoroacetoacetate of the formula (II). Alkylhydrazines can be used as a substance or preferably as an aqueous solution. For example, methylhydrazine is used as a 30-40% solution in water.

According to the present invention, it is essential that the reaction is performed in the presence of a solvent. Suitable solvents are: dialkyl ethers, cyclic ethers (THF, dioxanes), dichloromethane, dichloroethane or trichloroethane; nitriles such as acetonitrile, propionitrile, n- or i-butyronitrile. Particular preference is given to using methyl tert-butyl ether, THF, toluene and chlorobenzene.

The product is isolated by phase separation and removal of the solvent under reduced pressure. It is also possible to convert the solution of the product further without isolation after the phase separation.

The yield of the product is generally 90-95%, the regioselectivity 100%.

PREPARATION EXAMPLES

Example 1

1-Methyl-3-difluoromethyl-5-hydroxy-1H-pyrazole

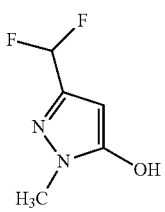

166 g (1 mol) of ethyl difluoroacetoacetate are initially charged in 500 ml of methyl tert-butyl ether, and 140 g of formic acid are added. After the mixture has been cooled to 5° C., 119 g of methylhydrazine are added in 40% aqueous solution. The mixture is stirred at 22° C. for a further 20 h. The phases are separated, and the organic phase is washed with 200 ml of water and dried over $MgSO_4$. After the solvent has been removed under reduced pressure, 148 g of the product are obtained as a yellow solid with an m.p. of 133° C. and a purity of 95%. Yield 95%.

Example 2

1-Methyl-3-difluoromethyl-5-hydroxy-1H-pyrazole 166 g (1 mol) of ethyl difluoroacetoacetate are initially charged in 500 ml of methyl tert-butyl ether, and 60 g of acetic acid are added. After the mixture has been cooled to 5° C., 119 g of methylhydrazine are added in 40% aqueous solution. The mixture is stirred at 22° C. for a further 20 h. The phases are separated, and the organic phase is washed with 200 ml of water and dried over $MgSO_4$. After the solvent has been removed under reduced pressure, 140 g of the product are obtained as a yellow solid with an m.p. of 133° C. and a purity of 96%. Yield 91%.

Examples 3

The Reaction According to WO 2007/013536

166 g (1 mol) of ethyl difluoroacetoacetate are initially charged in 400 ml of acetic acid. The mixture is cooled to 5° C. and 119 g of methylhydrazine are added as a 40% solution in water. The mixture is stirred at 22° C. for a further 20 h. The LC-MS shows 55 area % of product, 15 area % of the 2-methyl-3-difluoromethyl-5-hydroxy-1H-pyrazole isomer, and 30 area % of numerous by-products.

The invention claimed is:

1. A process for preparing a compound of formula (I)

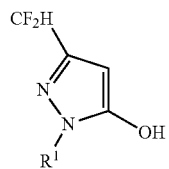

in which $R^1$ is a linear or branched $C_1$-$C_6$-alkyl group, comprising reacting a compound of formula (II)

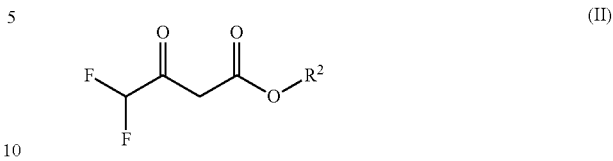

in which $R^2$ is a linear or branched $C_1$-$C_6$-alkyl group, with a compound of formula (III)

$$NH_2—NH—R_1 \quad (III)$$

in the presence of an organic acid and a solvent.

2. A process according to claim 1, wherein the organic acid is formic acid, acetic acid, p-toluenesulphonic acid or trifluoroacetic acid.

3. A process according to claim 1, wherein the compound of formula (II) is methyl difluoroacetoacetate or ethyl difluoroacetoacetate.

4. A process according to claim 1, wherein the compound of formula (III) is methylhydrazine or ethylhydrazine.

5. A process according to claim 1, wherein between 0.8 and 1.8 mol of the compound of formula (III) and 0.1 to 1.2 mol of the organic acid are used per mole of the compound of formula (II).

6. A process according to claim 1, wherein the solvent is selected from the group consisting of dialkyl ethers, tetrahydrofuran, dioxane, dichloromethane, dichloroethane or trichloroethane, acetonitrile, propionitrile, n- or i-butyronitrile, methyl tert-butyl ether, toluene and chlorobenzene.

7. A process according to claim 1, wherein the solvent is methyl tert-butyl ether.

8. A process according to claim 2, wherein compound of formula (II) is methyl difluoroacetoacetate or ethyl difluoroacetoacetate.

9. A process according to claim 2, wherein the compound of formula (III) is methylhydrazine or ethylhydrazine.

10. A process according to claim 3, wherein the compound of formula (III) is methylhydrazine or ethylhydrazine.

11. A process according to claim 2, wherein between 0.8 and 1.8 mol of the compound of formula (III) and 0.1 to 1.2 mol of the organic acid are used per mole of the compound of formula (II).

12. A process according to claim 3, wherein between 0.8 and 1.8 mol of the compound of formula (III) and 0.1 to 1.2 mol of the organic acid are used per mole of the compound of formula (II).

13. A process according to claim 4, wherein between 0.8 and 1.8 mol of the compound of formula (III) and 0.1 to 1.2 mol of the organic acid are used per mole of the compound of formula (II).

14. A process according to claim 2, wherein the solvent is selected from the group consisting of dialkyl ethers, tetrahydrofuran, dioxane, dichloromethane, dichloroethane or trichloroethane, acetonitrile, propionitrile, n- or i-butyronitrile, methyl tert-butyl ether, toluene and chlorobenzene.

15. A process according to claim 3, wherein the solvent is selected from the group consisting of dialkyl ethers, tetrahydrofuran, dioxane, dichloromethane, dichloroethane or trichloroethane, acetonitrile, propionitrile, n- or i-butyronitrile, methyl tert-butyl ether, toluene and chlorobenzene.

16. A process according to claim 4, wherein the solvent is selected from the group consisting of dialkyl ethers, tetrahydrofuran, dioxane, dichloromethane, dichloroethane or trichloroethane, acetonitrile, propionitrile, n- or i-butyronitrile, methyl tert-butyl ether, toluene and chlorobenzene.

17. A process according to claim 5, wherein the solvent is selected from the group consisting of dialkyl ethers, tetrahydrofuran, dioxane, dichloromethane, dichloroethane or trichloroethane, acetonitrile, propionitrile, n- or i-butyronitrile, methyl tert-butyl ether, toluene and chlorobenzene.

18. A process according to claim 2, wherein the solvent is methyl tert-butyl ether.

19. A process according to claim 3, wherein the solvent is methyl tert-butyl ether.

20. A process according to claim 4, wherein the solvent is methyl tert-butyl ether.

21. A process according to claim 5, wherein the solvent is methyl tert-butyl ether.

* * * * *